United States Patent
Friese et al.

(10) Patent No.: US 9,424,324 B2
(45) Date of Patent: Aug. 23, 2016

(54) METHOD, COMPUTER-READABLE MEDIUM, AND SYSTEM FOR STORING, ALLOCATING AND RETRIEVING MEDICAL IMAGE DATA IN A DISTRIBUTED COMPUTERIZED SYSTEM OF A CLINICAL FACILITY

(75) Inventors: Thomas Friese, Munich (DE); Thomas Haug, Herzogenaurach (DE); Stephan Merk, Munich (DE); Wolfgang Rueger, Neptune Beach, FL (US); Achim Scheidl, Nuremberg (DE); Matthias Senn, Erlangen (DE); Veerendra Shetty, Erlangen (DE)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 1188 days.

(21) Appl. No.: 12/437,650

(22) Filed: May 8, 2009

(65) Prior Publication Data
US 2010/0036879 A1    Feb. 11, 2010

(30) Foreign Application Priority Data

Aug. 8, 2008   (DE) .......................... 10 2008 037 094

(51) Int. Cl.
*G06F 17/30*   (2006.01)
*G06F 19/00*   (2011.01)

(52) U.S. Cl.
CPC .... *G06F 17/30575* (2013.01); *G06F 17/30265* (2013.01); *G06F 19/321* (2013.01); *G06F 17/30578* (2013.01)

(58) Field of Classification Search
CPC ................. G06F 19/321; G06F 19/322; G06F 17/30509; G06F 17/30578; G06F 17/30575
USPC ........................................... 707/999.103, 707
See application file for complete search history.

(56) References Cited

U.S. PATENT DOCUMENTS

| 2002/0001395 | A1* | 1/2002 | Davis et al. ............. 382/100 |
| 2002/0059243 | A1* | 5/2002 | Gillespie et al. ............ 707/10 |

(Continued)

OTHER PUBLICATIONS

Ozkan et al. "Neural-Network-Based Segmentation of Multi-Modal Medical Images: A Comparative and Prospective Study", Sep. 1993, IEEE Transactions on Medical Imaging, vol. 12, No. 3.*

(Continued)

*Primary Examiner* — Apu Mofiz
*Assistant Examiner* — Sheryl Holland
(74) *Attorney, Agent, or Firm* — Schiff Hardin LLP

(57) ABSTRACT

In a method for storing and providing medical image data in a distributed, computer-based system of a clinical facility comprising multiple satellites, wherein a satellite has at least one modality, an image administration server and at least one local database, and wherein the clinical facility also has a central database for the administration of the stored image data and a central long-term storage for long-term storage, the image data are acquired at the modality, the image data include metadata and pixel data, partial metadata in the metadata of the acquired image data are marked, at least the metadata of the image data acquired are locally stored at the respective satellites, the image data of the image data acquired at the respective satellites are centrally stored in the central long-term storage, all metadata stored in the local database in the central database are completely, centrally replicated, and the marked partial metadata of the image data from the central database are partially, automatically replicated at respective local databases of one, multiple or all satellites in order to be able to provide these image data at the satellites.

22 Claims, 3 Drawing Sheets

(56) References Cited

U.S. PATENT DOCUMENTS

| | | | |
|---|---|---|---|
| 2004/0034550 A1* | 2/2004 | Menschik et al. | 705/3 |
| 2004/0141661 A1* | 7/2004 | Hanna et al. | 382/305 |
| 2005/0071194 A1* | 3/2005 | Bormann et al. | 705/2 |
| 2005/0244082 A1 | 11/2005 | Yamatake | |
| 2006/0251292 A1* | 11/2006 | Gokturk et al. | 382/103 |
| 2007/0192352 A1* | 8/2007 | Levy | 707/102 |
| 2008/0016111 A1* | 1/2008 | Keen | 707/104.1 |
| 2008/0147860 A1* | 6/2008 | Edwards et al. | 709/225 |
| 2009/0132636 A1* | 5/2009 | Natanzon et al. | 709/201 |
| 2012/0070045 A1* | 3/2012 | Vesper et al. | 382/128 |

OTHER PUBLICATIONS

Martinez et al. "Design of Multimedia Global PACS Distributed Computing Environment", 1995, Hawaii International Conference on System Sciences.*
King et al., "Distributed Content-Based Visual Information Retrieval System on Peer-to-Peer Networks", 2004, ACM.*
"GE PACS Broker v2.0 (Modality Worklist Interfaces)", 2004, GE Medical Systems, General Electric.*
Siemens Brochure for SIENET MagicStore (1993).
Wikipedia: "Failover"; Wikipedia, free Encyclopedia; URL: http://en.wikipedia.org/w/index.php?title=Failover&oldid=204182212; p. 1; 2008; (accessed Jun. 25, 2015).

* cited by examiner

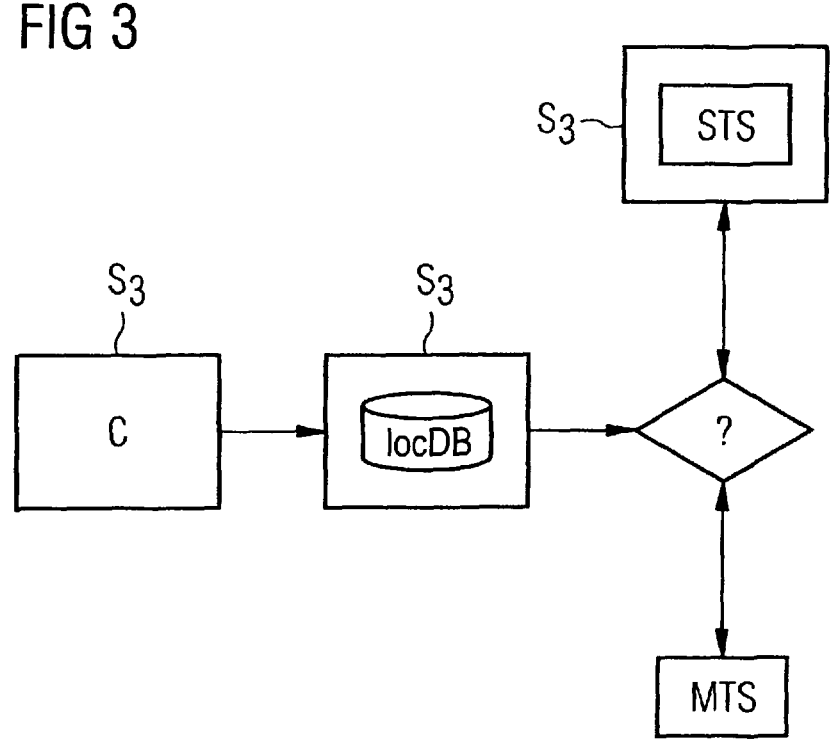

METHOD, COMPUTER-READABLE MEDIUM, AND SYSTEM FOR STORING, ALLOCATING AND RETRIEVING MEDICAL IMAGE DATA IN A DISTRIBUTED COMPUTERIZED SYSTEM OF A CLINICAL FACILITY

BACKGROUND OF THE INVENTION

1. Field of the Invention

The present invention is in the field of medical technology and concerns the storage organization of image data in a distributed system that comprises multiple clinical facilities that are engaged in data exchange with one another over a network.

2. Description of the Prior Art

Today clinical facilities normally have a number of departments, including satellites with a complete PACS (PACS=Picture Archiving and Communication System) with one or more modalities for the acquisition of medical image data or of other examination data (for example CT, MR, AX etc.), as well as with stores and databases, as well as management systems.

In such a distributed system (which can be a network of clinical facilities with multiple satellites that are distributed worldwide, for example), a very high data volume of medical image data is acquired, transferred and administered. High requirements for the storage organization with regard to storage space and access times result. With regard to the storage organization and data administration, it is also a significant requirement to enable an overview of all image data available in the distributed system from every satellite.

Moreover, a requirement exists in the medical field to ensure a high availability of the image data in the case of server, database or network failures.

The storage and archiving of examination data of a modality previously occurred only at specific databases within a satellite. In order to enable access spanning all satellites, it has been conventional to employ an administration and access layer at a higher abstraction level in the overall system. Which examination data are accessible and available at which satellites is administered in such an administration layer (which also includes databases). This has the disadvantage that a high administration expenditure is required in order to enable access over all satellites. A high level of availability can be realized only with difficulty.

A system known as the SIENET Magic Store System is commercially available from Siemens that has a Magic View component and a Magic Store component. The Magic Store component is always associated with one satellite and by default provides only information about data that are available at this satellite. The Magic Store component alone thus offers only a "local view" of the information or data. A "global view" is possible in this system only by the use of complicated ad hoc measures. All information with regard to examination data are stored and administered in two databases:

1. A patient directory (PDIR) contains all examination data sets for all patients (moreover, additional details with regard to a patient are stored here, for example patient name, birth date, gender, hospital department, patient identification number etc.)

2. An image management system database (IMS) is designed to stored image data with regard to the examinations. For example, this contains images of patients that are currently examined or that have been examined recently. In both databases (IMS, PDIR), searches have previously been conducted via queries in the event that workstations request specific data sets of specific patients.

The previous systems do not provide a satisfactory result (in particular due to the default limitation to the "local view") in satellite-encompassing accesses to examination data that are stored or, respectively, saved at different locations in a distributed system and which sometimes must also be accessed very quickly (in particular in the scope of a diagnosis or finding). The results also are not satisfactory with regard to a high degree of availability of the image data and the provision of an overview of all available image data in the distributed system, or such results could be achieved only with a high expenditure and high network utilization.

SUMMARY OF THE INVENTION

An object of the present invention is to improve access possibilities to examination data that are stored in a distributed multi-site system having multiple satellites, and in particular to be able to provide satellite-spanning access with optimal high availability and acceleration with optimally minimal design of the satellites. High availability means that the distributed multi-site system is robust with regard to network and/or database failures.

Moreover, with optimally low network utilization and administration cost, the storage of the image data should be organized such that a consistent and complete overview of all image data available in a distributed system can be provided from every satellite.

These objects are achieved by a method for storing and providing medical image data or images in a distributed, computer-based system of a clinical facility that has multiple satellites, wherein each satellite includes at least one imaging modality, an image administration server and at least one local database. The clinical facility also has a central database for the administration of the stored image data and a central long-term storage for long-term storage of the medical image data. The method includes the following method steps:

acquisition of the image data at the modality, wherein the image data comprise metadata and pixel data;

marking of partial metadata in the metadata of the acquired image data;

local storage in the local database of at least the metadata of the image data acquired at the respective satellites;

central storage in the central long-term storage of the image data of the image data acquired at the respective satellites in the central long-term storage [sic];

complete, central replication of all metadata stored in the local database in the central database;

partial, decentralized, automatic replication of the marked partial metadata of the image data from the central database at a respective local database of one, multiple or all satellites in order to be able to provide these image data at the satellites.

As noted, the method concerns the storage/provision of image data in a distributed system. This means the provision of logical or physical storage units and of data flows of the image data with access possibilities. In principle, all mentioned instances or modules (for example the local database or the central long-term storage, the imaging modality and the image administration systems, and the respective satellites) are connected among one another with respective clients (for example workstations and one or more central databases) via a communication network. The data flow here is advantageously based on the DICOM protocol on a foundation of suitable communication protocols. However, other protocols can also be used that are suitable for the transmission of the image data and are adapted to a format of the medical image data.

The medical image data are composed of pixel data and metadata. Metadata are typically stored in a header, for example in a DICOM header with regard to the pixel data or, respectively, the subject shown by the pixel data. The metadata are formed as hierarchically arranged data elements in the DICOM header. Patient data elements (for example name, patient ID, gender and insurance number etc.) are at the uppermost point of the hierarchy. The studies or series of data elements that, for example, designate the number of the series in a study series or, respectively, the count of the images in a series and include an identification number of the series or study and of the respective image datum are located at a second position. Furthermore, other data elements include information about the utilized modality. Further below in the hierarchy of the metadata are image data elements that, for example, contain the number of pixels, columns and resolution used, information about the resolution used and photometric data. Following the metadata are then the "actual" data, i.e. the pixel data. The pixel data are those data in the image data that enable a presentation of the image data for a human observer via a DICOM-capable viewer. For the invention, it is only necessary that the information be structured in the image data or be arranged with a better hierarchical structure or, respectively, can be structured (hierarchically) as necessary through corresponding transformations. The image data thus do not necessarily have to exist in a DICOM format. The method is naturally also not limited to image data. Other data (for example video, text and sound files) are encompassed within the scope of the invention.

The clinical facility can be a hospital with different departments or a clinic that has branches in different regions. The departments of the clinical facility here are designated as satellites, comprising a series of clients or workstations, medical modalities fashioned for the detection and acquisition of the medical image data, and a complete medical technology infrastructure such as a PACS system; data management server system, image data administration server (system) and a file server for the storage, replication and/or relaying of data in the communication network are defined. The file server can also be fashioned as a component of the image data administration server system or, respectively, be attached to this.

The imaging modality is a technology modality for the acquisition of medical image data, for example a computed tomography apparatus, a magnetic resonance apparatus, an ultrasound apparatus, etc. The modalities communicate with the image administration server via a DICOM interface. An RIS modality interface is upstream.

A replication of image data presumes that the image data are stored multiple times. The data thus are not merely moved from a first storage location to a second storage location; rather, they are stored redundantly, which increases the reliability of the system and also may improve the access speeds if the storage occurs in a local memory. Either the replication ensues directly via the image administration server or, respectively the replication ensues between the appertaining databases via a corresponding trigger signal distributed by the image administration server or by the databases. How or from which instance the replication occurs is insignificant to the invention, however. The replication of the metadata ensues partially or entirely depending on a direction of the replication. The replication of the metadata from the local databases in the central database ensues completely. The replication of the metadata from the central database in the local databases ensues partially so that only the marked, partial metadata are replicated in the local databases.

According to the invention, partial metadata are marked, for example by filtering the metadata. The marking or filtering is based on the hierarchical arrangement of the data elements from which the metadata are constructed. According to the invention, at which level in the hierarchy data elements should be filtered out (which data elements then form the partial metadata) can be configured. How "detailed" the information in the partial metadata should be in relation to the complete metadata can thus be controlled.

According to one aspect of the invention, the three uppermost data elements in the hierarchy (i.e. the patient data elements, the series and study data elements) are filtered out from the header of every acquired medical image. According to embodiment of the invention, up to which data element level in the hierarchy of the data elements the filtering occurs can be configured.

The partial metadata are then advantageously replicated from the central database into all the local databases of those satellites at which the respective medical image data were not acquired.

According to the invention, all complete metadata of all medical image data that were acquired anywhere in the medical facility are always stored in the central database, meaning that they are locally available at the satellites (in contrast to the partial metadata).

Generally, the local databases contain only partial metadata of the image data acquired anywhere in the medical facility. The local databases may also contain complete metadata, but only of those image data that were actually acquired at the respective local modality of the respective satellite.

In this way the local databases can be kept relatively thin and narrow-dimensioned since they just do not have to comprise all metadata of all medical image data of the medical facility.

The partial metadata of all medical image data allow a consistent view of or, respectively, browsing through all medical image data available anywhere in the medical facility.

This is enabled by the metadata always being entirely "uploaded" (i.e. centrally replicated) from the local databases of all satellites into the central database while the metadata are only partially "downloaded" in the opposite direction (thus from the central database into the local databases)—in this case the replication thus occurs partially and in a decentralized manner. Because only partial metadata are replicated in the "download" direction, this can also be designated as a "partial replication of the partial metadata".

In the search for necessary medical image data, medical personnel at the respective satellites thus only need to respectively direct queries to the local database in order to obtain information about whether the sought image data are present in the first place, and second whether they are present locally or non-locally within the medical facilities.

After this information has been obtained by querying the local database, the pixel data of the sought medical image data can be loaded and provided from (for example) the central long-term storage using a reference information for the storage location of the pixel data, which reference information is associated with the metadata in the central database. A query to the central database thus occurs only when the image data must be loaded from the central long-term storage since the image data were not locally acquired at the querying satellite.

According to one aspect of the invention, the pixel data are stored in the central long-term storage and/or in the central short-term storage in a format that is suitable to enable a direct access to the pixel data. In particular, the pixel data are kept uncompressed or only slightly compressed (for example in 10-fold compression) in the central short-term storage. The image data can be viewed more quickly by the satellites given a load request, which positively affects the workflow, particularly in emergency situations.

According to an embodiment of the invention, the satellites have a local, short-term storage (STS). The pixel data of the image data acquired at the respective satellites can optionally be stored not directly and centrally but rather locally in the short-term storage of the satellite. According to the "locality of reference principle", it is probable that locally acquired image data will be increasingly accessed by the local medical personnel in the future. The image data can thereby be loaded more quickly, and it leads to a decrease of the facility-wide data traffic and thus to an unloading of the network.

A full utilization of the communication network can also be kept to a minimum in this way since for the most part only partially metadata are replicated within the network.

According to another embodiment of the invention, if the facility has additional central databases, the metadata are replicated between the central database and the additional central databases. The complete metadata are hereby replicated. The facility can be designed to be even more robust with regard to failures via this decentralization of the storage of the complete metadata.

According to the invention, the feature that every satellite possesses at least partial metadata of all medical image data of the medical facility allows it to provide an information provisioning that is robust with regard to network failures.

Through the local database the medical personnel can locally obtain information at each satellite about whether medical image data for a patient are present at all and where they are stored. The medical personnel can then obtain more detailed information about the desired image data via alternative telecommunication channels (for example the telephone) in the event of a network failure (for example) that precludes a retrieval of the corresponding medical image data from the central long-term storage. For example, the treating physician who is located at one of the other satellites and who initiates the acquisition of this sought medical image data can be specifically contacted in this way.

The above object lies also is achieved in accordance with the invention by a method for loading medical image data that comprise metadata and pixel data into a distributed, computer-based system of a clinical facility having multiple satellites, wherein each satellite has at least one imaging modality, an image administration server and at least one local database, and wherein the clinical facility has a central database for the administration of the stored image data and a central long-term storage for long-term storage, with the steps of determining whether the image data to be loaded are present locally at the satellite (S), and, if so, loading the image data by accessing the local database, and otherwise loading the image data from the central long-term storage by accessing the central database.

In an embodiment of the method according to the invention, the satellites each have a short-term storage for storing the medical images that were acquired at the respective satellites. A storage location of the medical image data to be loaded is also determined using the metadata or the partial metadata and, depending on this determined storage location, the medical image data are loaded either from the local short-term storage or from the central long-term storage.

Before the actual loading of the images, in principle a query is first transmitted to the local database at each satellite. The partial metadata offer "enough" information with regard to an existence and information down to the series level. If only partial metadata are present, the associated pixel data are not locally available. The storage location of the pixel data of the image data can then be determined via the associated (complete) metadata or the reference information in the central database that is associated with these metadata. Questions with regard to the existence of the image data and information about the image data up to the series level can thus be answered according to the invention without having to already load the network here. Only if the image data are not present in the local short-term storage does the loading occur from the central long-term storage using the reference information for the storage location of the pixel data that are associated with the (complete) metadata in the central database. An information yield with regard to the existence and/or location (locally present or not present) is thus maximized, and the network load is minimized at the same time.

In another embodiment of the method according to invention, the local databases are fashioned as a failover cluster. If the distributed system has multiple additional central databases, the central databases are also alternatively or additionally fashioned as failover clusters. The term "failover" or "failover function," means the unplanned switching from a "primary server" to a second "secondary server". The central or local databases in their respective clusters thereby take over the respective failover functions in addition to their respective normal, local or central functions. The system according to the invention therefore manages without dedicated or specific failover servers.

In the event that one or more of the central databases or one or more of the local databases are not available, the determination of the presence and/or of the storage location of the image data can ensue using the metadata and/or the partial metadata in those central databases or local databases that are available. The system is high-performance because it has high availability.

In the above object also is achieved in accordance with the invention by a system for the storage of medical images in a computer-based clinical facility that comprises multiple satellites, wherein each satellite has at least:
 a modality for the acquisition of the image data;
 an image administration server for the management of the image data;
 a local database;
 and wherein the system additionally has:
 a central database to administer the stored image data;
 a central long-term storage for long-term storage;
 a file server that replicates and/or relays the image data acquired by the modality;
 a filter unit that is designed to filter partial metadata out from metadata of the medical images.

The file server is designed to store pixel data of the image data locally acquired by the respective modality in the central long-term storage; and to store the metadata of the locally acquired image data in the local database; and to completely replicate the said locally acquired image data from the local database in the central database. The filtered-out partial metadata are replicated automatically or upon request by one of the satellites from the central database to the respective local databases of all those satellites at which the medical images were not acquired.

This replication advantageously ensues automatically. Alternatively, the replication ensues only upon request.

According to one aspect of the invention, the system has additional central databases, and the metadata are replicated between the central database and the additional central databases. This increases the robustness of the system with regard to local failures.

According to one aspect of the invention, the central database and/or the additional central databases and/or the local databases is/are respectively fashioned as a failover cluster in order to maintain high availability of the image data in the system.

In an embodiment of the invention, the central databases and/or the additional central databases are attached at one or more of the respective satellites. The necessity of constructing specially modified infrastructures (for instance "database sites") is avoided since the existing infrastructure of the satellites can be used. This also allows the formation of entities known as main sites, i.e. satellites at which a central database is attached. It is then provided that every main site supplies a specific number of satellites without central databases with the partial metadata. The replication of the partial metadata in the respective local databases thus ensues in the framework of a cluster structure. A main site with a specific number of satellites, to at which no central database is attached, forms a cluster in the distributed system.

An additional achievement of the object lies in a method in which the access times to the image data in the distributed system are additionally improved by means of targeted caching. This method can be used in combination with or independent of the method according to the invention that was described above.

This object of improved access times is in particular achieved in accordance with the present invention by a method for storage organization for medical image data or images in a distributed, computer-based system of a clinical facility having multiple satellites; wherein each satellite has at least one modality for image data acquisition, one PACS system and at least two local short-term stores with different access speeds, in particular a cache with fast access and a short-term storage with a slower (in comparison to the cache) access, wherein the clinical facility has a central database for the administration of the stored image data and a central long-term storage for long-term storage of image data. The method includes the following steps:
  acquiring the image data at an imaging modality;
  selecting relevant image data from the set of the acquired image data;
  locally storing the relevant image data in the cache;
  locally replicating all acquired image data in the short-term storage;
  centrally replicating all acquired image data in the long-term storage;
  decentrally, automatically distributing to a respective, local memory of all satellites for the purposes of storing the relevant image data at a respective local storage of all satellites so that an access to remotely acquired or stored image data can be provided at a respective satellite, wherein the modality is fashioned with at least one physical cache and with at least one auxiliary functionality that is executed by the modality when a pre-configurable load limit is exceeded for the short-term storage locally associated with the modality.

The above object also is achieved by an additional system for storing medical images in a computer-based clinical facility that has multiple satellites, wherein a satellite has at least one imaging modality to acquire the image data;
a PACS system to administer and manage data; and
two local short-term storage modules, in particular a cache and a short-term storage; and wherein the clinical facility has:
  a central database to administer the stored image data;
  a central long-term storage for long-term storage;
  a file server that stores, replicates and/or relays image data acquired by the modality; and
  a selection module that is designed to select relevant image data from the set of the acquired image data; wherein the file server is designed to locally store the image data registered as relevant by the selection module in the cache, and to locally replicate all image data acquired by the modality in the short-term storage, and to centrally replicate all image data acquired by the modality in the long-term storage, and which file server automatically, decentrally distributes the image data registered as relevant by the selection module to all other satellites, in particular to the respective local stores of the respective satellites so that an access to remotely acquired or stored image data is enabled at a respective satellite, and wherein the modality is fashioned with at least one auxiliary module; that executed in the modality when a specific functionality in the short-term storage that is locally associated with the modality cannot be executed because the short-term storage has exceeded a pre-configurable load limit; wherein the auxiliary module is designed to execute an additional functionality.

The auxiliary module is fashioned to execute at least one auxiliary functionality. This advantageously includes a relaying or sending of image data to other storage regions or, respectively, instances. However, in principle all functionalities that the short-term storage provides can also be formed as an auxiliary functionality. The auxiliary functionality is executed on the part of the modality when it is established that the short-term storage that is associated with the respective modality has exceeded a pre-configurable load limit. In other words, the modality can also take over functions or, respectively, tasks from the short-term storage when this is overloaded, for example because too many workplaces have corresponding requests with image load jobs. The load limit can be dynamically adapted and can be preset. Metadata that record a utilization of the involved instances (in particular of the short-term storage) are acquired in the communication between modality and short-term storage.

For those skilled in the art it is clear that a data exchange is provided between all participating modules, and in particular between the satellites.

In an advantageous development, the system can additionally comprise an accumulator that is fashioned as a cache.

The modality of the system can also additionally be fashioned with a physical cache that enables a fast access to local image data.

It is noted again here that the features mentioned in connection with the method can likewise be applied to the system, the computer program product and/or the storage medium, wherein the functionalities are fashioned via corresponding modules that are designed to execute the corresponding functionality.

The embodiments of the method according to the invention that are described in the preceding can also be fashioned as a computer program product (computer-readable medium), wherein the computer is operated to implement the method according to the invention as described in the preceding by program code stored by the computer-readable medium being executed by a processor.

BRIEF DESCRIPTION OF THE DRAWINGS

FIG. 3 schematically illustrates a data flow upon loading of image data in accordance with the invention.

DESCRIPTION OF THE PREFERRED EMBODIMENTS

Figure 1:
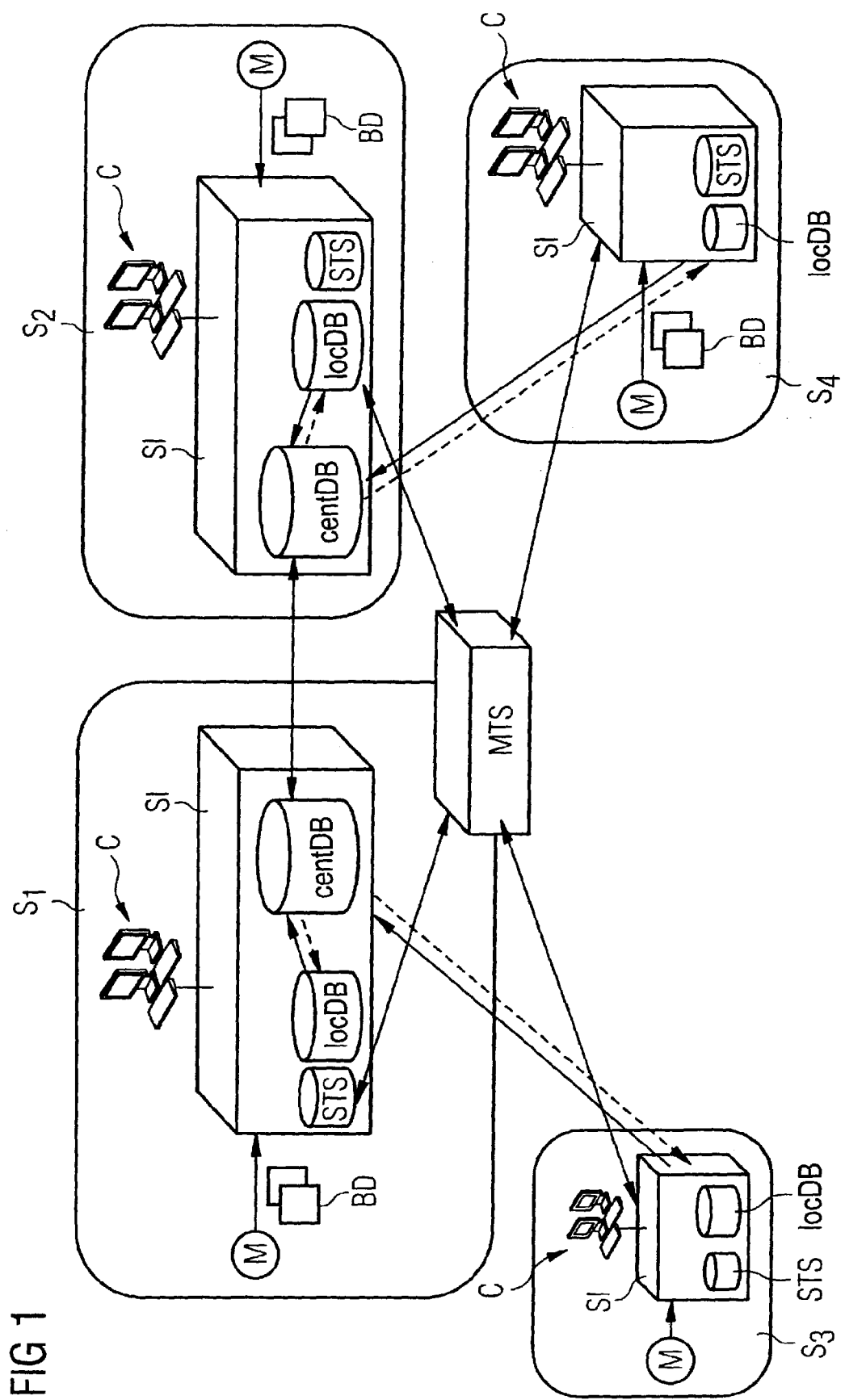
FIG. 1 is an overview depiction of modules with associated storage units according to a preferred embodiment of the invention.

The schematic design of a clinical facility that consists of a plurality of satellites S is shown in FIG. 1. Four satellites S1, S2, S3 and S4 are presented in FIG. 1. The satellites S1 and S2 exemplarily characterize two main sites.

A satellite S comprises at least one modality M for the acquisition of the image data BD. The image data BD are recorded or acquired in a DICOM format. The image data include metadata and pixel data. The metadata in turn comprise data elements that are hierarchically arranged and include respective information about a patient that is associated with the image data; information about the series to which the image data belong; and information as to which study these series belong. Moreover, the metadata contain a unique ID that is associated with each of the image data upon acquisition at the modality.

Moreover, the satellite S has a short-term storage STS that can be a cache. The short-term storage STS can be fashioned as a RAID (Redundant Array of Independent Disks). An image administration server SI is additionally provided at each of the satellites, which image administration server SI comprises or, respectively, controls a file server and a web server (both are not shown). The image administration server SI provides storage space for larger data sets (in particular the image data BD) and enables multiple users to access these data over a network. Moreover, the image administration server SI coordinates an image data traffic between and within the satellites S. The file server can also be called a data file server and has hardware (for example in the form of hard disks) in combination with software that regulates access modalities.

The short-term storage STS serves for the storage of the image data BD that were acquired at the respective satellites S.

Furthermore, a local database locDB (that can be set up as a relational database, for example) is associated with each satellite S. The local database locDB serves to store all metadata of all those image data BD that were acquired via the respective modality at the respective satellite S. For example, the metadata can be obtained from the image data via a corresponding "grabber" or via a filter tool and, as an ASCII character string, be imported into the local database as data sets. This functionality can be provided via the image administration server SI or directly by a database server (not shown) of the local database locDB. According to the invention, the local databases also serve to store partial metadata of all medical images available on the network, as is explained in detail further below in connection with the mode of operation of the system.

Central databases centDB are also attached to the satellites S1 and S2 (set up as main sites) in addition to the respective local databases locDB, but, this is only an example. The central database centDB could also run at independent, special "database satellites".

The central databases centDB are also set up as relational databases and attached to the main sites S1 and S2. In contrast to the local databases locDB, all metadata of all image data that were acquired at any modality M at any of the satellites S of the medical facility are stored here.

The metadata are regularly replicated between the central databases via known replication mechanisms as they are known from the field of data technology. This replication can be coordinated by the image administration server SI.

The two central databases centDB can additionally be fashioned as a failover cluster so that the respective other central database is automatically available in the case of the failure of one of the central databases centDB.

Filtering devices to mark the partial metadata by filtering out data elements up to a configurable hierarchy level (starting from the patient data element) are provided at the central databases of the main sites S1 and S2. How much "detailed knowledge" about all image data available on the network should be at the local databases locDB thus can be defined.

A number of clients C are connected to the satellites S mentioned in the preceding. Alternative embodiments of a satellite S provide additional modules here, for example an administration management (operation management—OPM) system with which, for example, the one-to-one correspondence of patient IDs and an image data ID is ensured across a facility.

All satellites S have access to a long-term storage MTS (as shown in FIG. 1) that, for example, is fashioned as a NAS system (Network Attached Storage) for satellite-spanning storage of image data. In contrast to conventional LTS long-term storage (which is more likely to be designated as an LTS archive wherein data are assembled or archived in a bundled archive format, for example via TAR or ZIP operations), however, the pixel data of the image data here are provided in an uncompressed or only very slightly compressed form. The image data BD are thereby quickly and directly available when the pixel data of the image data BD are requested by one of the clients C at one of the satellites since no de-archiving is required. In this sense the long-term storage MTS can be thought of as a "medium term storage" system.

The long-term storage MTS according to the invention is also to be viewed as an extension of the archive function of the LTS archive (not shown in FIG. 1). While the image data BD are not deleted in a conventional LTS archive, this is by all means the case in the long-term storage MTS insofar as it is ensured that the image to be deleted is archived in the LTS archive. A holding duration of the long-term storage MTS according to the invention thus lies between that of the STS and that of the LTS archive. The pixel data of the image data BD are advantageously compressed in a visually lossless manner in the long-term storage MTS, meaning that these are also usable in a compressed state for medical purposes.

In an embodiment of the invention, the degree of compression for the pixel data is configurable in the long-term storage MTS—i.e. "uncompressed" through "visually lossless" to "lossy"—depending on the application purpose of the image data BD.

The long-term storage MTS is arranged at a central location in FIG. 1 and communicates with the respective connected satellites S. The local pixel data of the image data BD of the individual satellites S that are stored in the short-term storage STS are regularly replicated at the central long-term storage MTS according to configurable "policies". For example, a replication always occurs when new image data have been acquired at one of the satellites S. All pixel data of all image data BD that were acquired by means of the respective modality at any of the satellites are thus available in the long-term storage MTS.

Moreover, the respective satellites S are engaged in a data exchange with one another. Clients C that access the image data BD are set up at the respective satellites.

Figure 2:
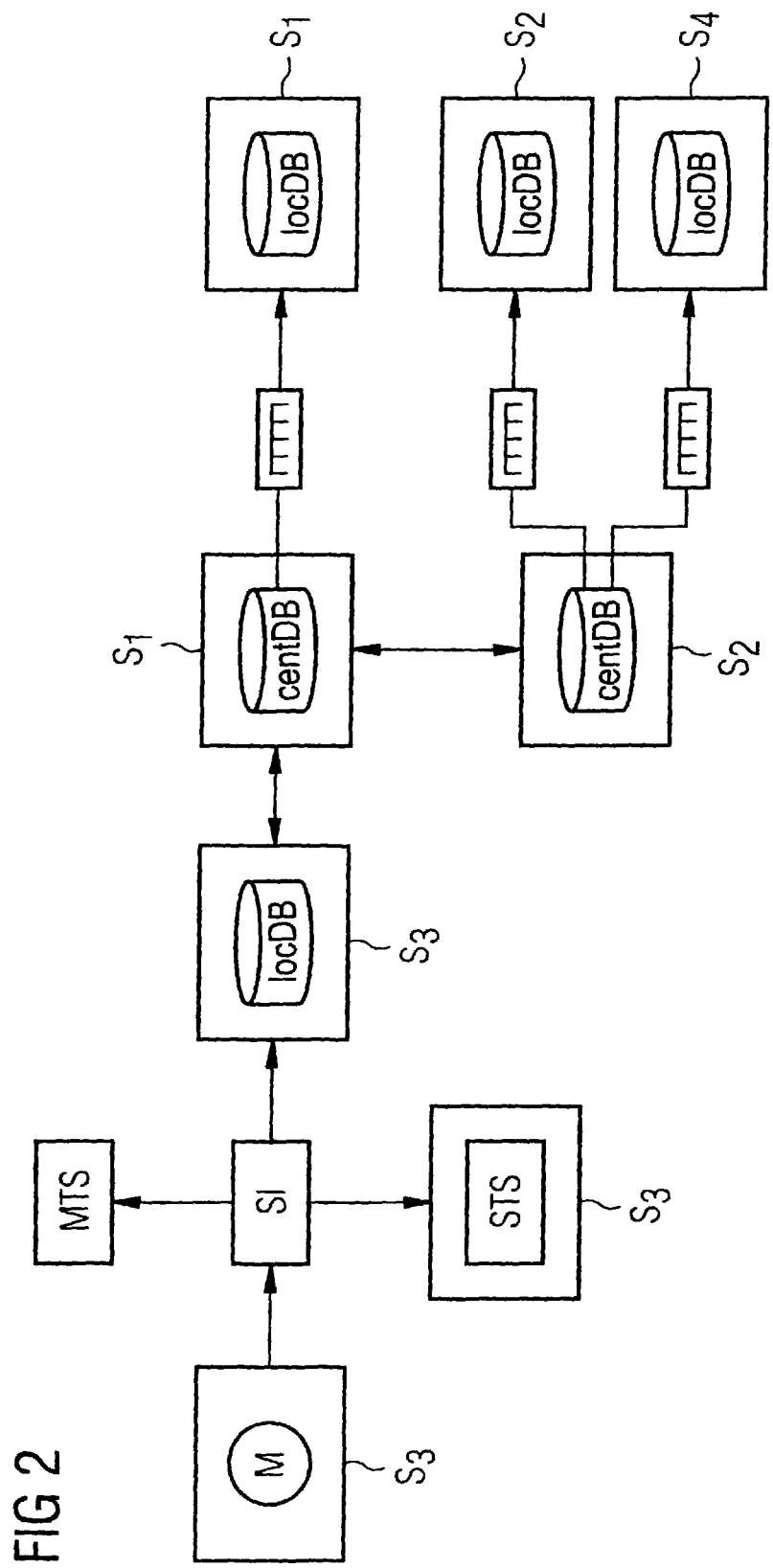
FIG. 2 schematically illustrates a data flow upon storage of image data in accordance with the invention.

A data flow according to the invention for the storage of the image data BD in a distributed system of the medical facility are schematically shown in FIG. 2.

The method according to the invention for the storage of the image data BD should be presented in the following in an example of satellite $S_3$. However, it is to be understood that the explanation of the method according to the invention using satellite $S_3$ is merely an example and can be analogously transferred to the other satellites $S_2$ through $S_4$. In the following it is assumed that, as shown in FIG. 1 and FIG. 2, the satellites S respectively possess local short-term storages STS. The method according to the invention would, however, also be conceivable without the local short-term storage STS, such that the pixel data of the image data are always stored centrally in one or more long-term storages MTS.

The image data BD are acquired as DICOM image data at the modality M of the satellite S3. The image administration server SI then initiates the storage of the pixel data of the acquired image data BD in the local short-term storage STS. The metadata of the acquired image data BD are thereupon deposited in the local database locDB as a data set by the image administration server SI. The pixel data of the acquired image data BD are subsequently stored in the long-term storage MTS. A storage location of the pixel data in the long-term storage MTS of the acquired image data BD is thereupon inserted into or associated with the previously-stored data set of the metadata, for example in the form of an address or a link or other suitable reference information in the local database locDB. Here the associated pixel data regarding the archived metadata are stored can thereby be learned from the local database locDB.

A central replication of the metadata of the acquired image data BD in the central database centDB of the satellite S1 at the main site subsequently ensues. Given central replication, the aforementioned reference information for the storage location of the pixel data are also replicated in the central databases. This replication can either be triggered by the image administration server SI or directly by the respective local database locDB.

The metadata in the central database centDB are then replicated in the other central databases centDB of the main site (exemplarily according to FIG. 1) of the satellite S2.

Finally, partial metadata from the metadata are then marked in the central databases centDB. The marked partial metadata are subsequently partially replicated from the central databases centDB S1 and S2 of the main sites to all local databases locDB of those satellites S at which the medical image data BD were not acquired. In particular, given this partial replication the reference information for the storage location of the pixel data is not replicated. This reference information then only ever exists in the central database centDB and locally only in the local databases locDB of those satellites S at which the image data BD were originally acquired.

It is thus ensured that "enough" metadata are present at all local databases locDB of the respective satellites S so that a facility-wide browsing of or, respectively, search for all the image data BD available in the medical facility is enabled. If the pixel data of the image data BD should then actually be accessed, this occurs using the corresponding reference information in the central database centDB.

A data flow according to the invention given loading of the medical image data BD in the distributed system of the medical facility should be schematically presented in FIG. 3.

The method according to the invention given the loading of the medical image data BD is again schematically presented as an example with regard to the satellite $S_3$.

The client C at the satellite $S_3$ initiates the loading of medical image data BD via a request to the local database locDB. The request is transmitted to the local database locDB via the image administration server SI, for example.

Using the metadata in the local database locDB, a presence of the requested medical image data BD can initially be determined. If the query to the local database locDB yields a data set with correspondingly matching metadata, the requested medical image data BD are locally "on hand" at the short-term storage STS. The image data BD can then be loaded (for example via the image administration server SI using the reference or storage location address associated with the metadata) and transmitted to the requesting client C for further processing.

However, if the query yields that the corresponding metadata exist only as partial metadata, the requested medical image data BD are not locally "on hand". In this case a request is transmitted to the central database in order to arrive at the reference information for the storage location of the pixel data of the image data BD that is associated with the complete metadata there. By means of this reference information, the pixel data are then requested from the central long-term storage MTS via the local image administration server SE and finally are transmitted to the requesting client C.

If the image data BD that were not originally acquired by the local modality of the requesting satellite S3 should thus be loaded, the partial metadata in the local database locDB provide only information about the image data BD up to the configured level—here thus the series level. For the concrete storage location of the pixel data, the reference information of the storage location must thus be obtained via a query to the central database centDB. Only then in this instance does a person have the complete information about the image data BD (complete metadata and reference information for the storage location of the pixel data) for a loading from the long-term storage MTS.

According to one embodiment, it is also provided for a "cross-loading" of the pixel data from other satellites S to be possible. In this case this additional storage location information of the satellites S holding the images ready would then be associated with the metadata in the central database DB. In particular, this storage location information points to the short-term storage STS of the satellite S at which the image data BD were originally acquired. In other words, in this embodiment it is not necessary to always load the pixel data from the long-term storage MTS. The pixel data can also be loaded from the satellite S at which the image data BD were acquired. This additional functionality of "cross-loading" allows a loading of the images BD even when the central database centDB is overloaded.

According to the invention, the distributed system according to the invention makes it more robust with regard to network and database failures in that not only are the central databases centDB organized as a failover cluster, but (additionally or alternatively) also the set of all local databases locDB and/or the set of the image administration servers SI at the respective satellites S.

According to an additional embodiment of the invention, it is ensured that the local databases locDB are automatically updated at the respective satellites S in the event of a network failure or the data sets of the local databases are updated as soon as the network connection is reestablished. This is important since generally new medical image data BD are acquired at the other satellites in the time in which the affected satellite S is offline.

The data set in the local database locDB that is attached to the offline satellite thus threatens to become obsolete very quickly. The replication via the central database centDB to the local database locDB of the offline satellite therefore automatically starts as soon as an online state of the affected offline satellite is detected (via known heartbeat technologies, for example).

The specification of the invention and the exemplary embodiments are not limited with regard to a specific physical realization of the invention. Those skilled in the art will understand that the invention can be realized partially or entirely in software and/or hardware and/or can be distributed on multiple physical products—in particular also computer program products.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for storing and providing medical image data in a distributed, computer-based system of a clinical facility comprising a plurality of satellites, wherein each satellite comprises at least one imaging modality, an image administration server, and a local database, and wherein said clinical facility further comprises a central database configured for administration of stored image data and a central long-term storage for long-term storage of said image data, comprising:
   acquiring image data at an imaging modality of a satellite of the plurality of satellites, said image data comprising metadata and pixel data, wherein the metadata includes hierarchically arranged data elements that include a patient data element having information corresponding to a patient associated with the corresponding image data, a study or series data element that identifies a study or series associated with the corresponding image data, a modality data element having information about an imaging modality associated with the image data, and an image data element having pixel data information associated with the corresponding image data;
   centrally storing, in said central long-term storage, the acquired image data and image data acquired at all other satellites of the plurality of satellites;
   locally storing the metadata of the image data acquired at the satellite in the local database of the satellite;
   in said central database, centrally replicating the metadata of the image data acquired at the satellite and metadata stored in the respective local databases of the other satellites of the plurality of satellites;
   filtering the replicated metadata corresponding to the image data acquired at the satellite to remove one or more of the data elements of the replicated metadata corresponding to the image data acquired at the satellite to generate partial metadata that corresponds to the image data acquired at the satellite and includes a subset of the data elements of the corresponding replicated metadata, wherein the filtering the replicated metadata includes determining a hierarchy level of the hierarchically arranged data elements of the replicated metadata, and removing the one or more data elements from the replicated metadata up to the hierarchy level of the hierarchically arranged data elements; and
   at the respective local databases of the other satellites of the plurality of satellites, acquiring and replicating, in a decentralized replication procedure, the partial metadata corresponding to the image data acquired at the satellite from the central database, and storing the replicated partial metadata in the respective local databases of the other satellites of the plurality of satellites.

2. A method as claimed in claim 1, wherein said central database of said clinical facility is a first central database, and wherein said clinical facility comprises a second central database, and comprising additional replicating the data among said first and second central databases.

3. A method as claimed in claim 2, comprising placing said second central database in communication with the plurality of satellites.

4. A method as claimed in claim 1, wherein each of the plurality of satellites comprises a local short-term storage, and comprising storing the pixel data of the image data acquired at the satellite in the local short-term storage of the satellite.

5. A method as claimed in claim 1, comprising storing the pixel data in a format enabling direct access to said pixel data.

6. A method as claimed in claim 1, wherein the filtering the replicated metadata corresponding to the image data acquired at the satellite comprises:
   marking one or more of the data elements of the replicated metadata corresponding to the image data acquired at the satellite based on the hierarchical arrangement of the data elements of the replicated metadata; and
   removing the one or more marked data elements from the replicated metadata corresponding to the image data acquired at the satellite to generate the partial metadata that corresponds to the image data acquired at the satellite.

7. A method as claimed in claim 1, comprising, at one or more of the other satellites of the plurality of satellites, determining the image data is not locally accessible from a respective local database of the one or more other satellites based on the storage of the replicated partial metadata corresponding to the image data acquired at the satellite in the respective local database of the one or more other satellites.

8. A method as claimed in claim 1, comprising, at said imaging modality of said satellite of the plurality of satellites, providing an auxiliary module and augmenting functions of the local database for short-term storage if a short-term storage capacity of said local database has exceeded a predetermined limit.

9. A method as claimed in claim 1, further comprising: designating one or more local databases of one or more of the plurality of satellites as a failover cluster and cross-loading image data from one or more other satellites of the plurality of satellites to said failover cluster, without said image data proceeding through said central long-term storage, when said central long-term storage is overloaded or otherwise unavailable.

10. A method as claimed in claim 1, wherein the patient data element, the study or series data element, the modality data element, and the image data element are arranged from highest to lowest in the hierarchy, respectively.

11. A method as claimed in claim 1, wherein the replicated partial metadata corresponding to the image data acquired at the satellite is indicative to the other satellites of the plurality of satellites that the image data associated with the replicated partial metadata was not locally acquired by corresponding imaging modalities of the other satellites of the plurality of satellites.

12. A non-transitory, computer-readable storage medium encoded with programming instructions for storing and providing medical image data in a distributed, computer-based system of a clinical facility comprising a plurality of satellites, wherein each satellite of the plurality of satellites comprises at least one imaging modality, an image administration server, and a local database, and wherein said clinical facility further comprises a central database configured for administration of stored image data and a central long-term storage for long-term storage of image data acquired at an imaging modality of at least one of the plurality of satellites, said image data comprising pixel data and metadata including data elements, said programming instructions causing processors in said system to:

locally store, in the local database of a satellite of the plurality of satellites at which the image data was acquired, metadata corresponding to the image data acquired at the satellite of the plurality of satellites;

in said central long-term storage, centrally store the image data acquired at the satellite and image data acquired at all other satellites of the plurality of satellites;

in said central database, centrally replicate the metadata of the image data acquired at the satellite and metadata stored in the respective local databases of the other satellites of the plurality of satellites;

filter the replicated metadata corresponding to the image data acquired at the satellite to remove one or more of the data elements of the replicated metadata corresponding to the image data acquired at the satellite to generate partial metadata that corresponds to the image data acquired at the satellite and includes a subset of the data elements of the corresponding replicated metadata, the data elements including a patient data element that includes information corresponding to a patient associated with the corresponding image data, a study or series data element that identifies a study or series associated with the corresponding image data, a modality data element that includes information about an imaging modality associated with the image data, and an image data element that includes pixel data information associated with the corresponding image data, wherein the data elements are hierarchically arranged and the filtering of the replicated metadata includes determining a hierarchy level of the hierarchically arranged data elements of the replicated metadata, and removing the one or more data elements from the replicated metadata up to the hierarchy level of the hierarchically arranged data elements; and at the respective local databases of the other satellites of the plurality of satellites, acquire and replicate, in a decentralized replication procedure, the partial metadata corresponding to the image data acquired at the satellite from the central database, and store the replicated partial metadata in the respective local databases of the other satellites of the plurality of satellites.

13. A method for storing and providing medical image data in a distributed, computer-based system of a clinical facility comprising a plurality of satellites, wherein each satellite of the plurality of satellites comprises at least one imaging modality, an image administration server, and a local database, and wherein said clinical facility further comprises a central database configured for administration of stored image data and a central long-term storage for long-term storage of said image data, comprising the steps of:

in a processor, determining whether metadata stored in said local database of said satellite corresponding to image data to be loaded is partial metadata, wherein the metadata stored in the local database of the satellite corresponding to that image data includes hierarchically arranged data elements and the partial metadata includes a subset of the data elements included in the corresponding metadata stored in the local database, said partial metadata being generated by removing one or more of the data elements from the corresponding metadata stored in the local database through a filtering process that includes determining a hierarchy level of the hierarchically arranged data elements, and removing the one or more data elements from the corresponding metadata stored in the local database up to the hierarchy level of the hierarchically arranged data elements, wherein the hierarchically arranged data elements include a patient data element having information corresponding to a patient associated with the corresponding image data, a study or series data element that identifies a study or series associated with the corresponding image data, a modality data element having information about an imaging modality associated with the image data, and an image data element having pixel data information associated with the corresponding image data;

determining, in said processor, whether said image data to be loaded is locally stored at the satellite based on the determination whether the metadata stored in said local database is partial metadata, wherein a partial metadata determination is indicative of the image data to be loaded having been acquired by the imaging modality of another one of the plurality of satellites different from the satellite, and wherein a metadata determination is indicative of the image data to be loaded having been acquired by the imaging modality of the satellite;

when said image data to be loaded is locally stored at a satellite, load the image data at that satellite by accessing the local database thereof; and when said image data to be loaded is not locally stored at the satellite, loading the image data from the central long-term storage by accessing said central database.

14. A method as claimed in claim 13, wherein at least some of said plurality of satellites each have a short-term storage, and comprising:

in satellites having a short-term storage, storing the pixel data of the image data acquired at that satellite in the short term storage of that satellite; and loading the image data from the short-term storage or from the central long-term storage based on a storage location that is determined using the metadata.

15. A method as claimed in claim 13, wherein said central database is a first central database and wherein said distributed system comprises a plurality of additional central databases, and wherein each of said first central database and said multiple additional central databases is configured as a failover cluster allowing storage of said image data therein if any of said first or additional central bases is not available for storage of said image data therein.

16. A non-transitory, computer-readable storage medium encoded with programming instructions for storing and providing medical image data in a distributed, computer-based system of a clinical facility comprising a plurality of satellites, wherein each satellite comprises at least one imaging modality, an image administration server, and a local database, and wherein said clinical facility further comprises a central database configured for administration of stored image data and a central long-term storage for long-term storage of said image data, said programming instructions causing processors in said system to:

determine whether metadata stored in said local database of said satellite corresponding to image data to be loaded is partial metadata that corresponds to metadata, wherein the metadata stored in the local database of the satellite corresponding to that image data includes hierarchically arranged data elements and the corresponding partial metadata includes a subset of the data elements included in the corresponding metadata stored in the local database, said partial metadata being generated by removing one or more of the data elements from the corresponding metadata stored in the local database through a filtering process that includes determining a hierarchy level of the hierarchically arranged data elements, and removing the one or more data elements from the corresponding metadata stored in the local database up to the hierarchy level of the hierarchically arranged data elements, wherein the hierarchically arranged data elements include a patient data element having information corresponding to a patient associated with the corresponding image data, a study or series data element that identifies a study or series associated with the corresponding image data, a modality data element having information about an imaging modality associated with the image data, and an image data element having pixel data information associated with the corresponding image data;

determine whether said image data to be loaded is locally stored at the satellite based on the determination whether the metadata stored in said local database is partial metadata, wherein a partial metadata determination is indicative of the image data to be loaded having been acquired by the imaging modality of another one of the plurality of satellites different from the satellite, and wherein a metadata determination is indicative of the image data to be loaded having been acquired by the imaging modality of the satellite;

when said image data to be loaded is locally stored at a satellite, load the image data at that satellite by accessing the local database thereof; and when said image data to be loaded are not present locally at the satellite, load the image data from the central long-term storage by accessing said central database.

17. A system for the storage of medical images in memory in a computer-based clinical facility that comprises a plurality of satellites, wherein a satellite of the plurality of satellites comprises:

a modality for the acquisition of the image data, the image data including pixel data and metadata having hierarchically arranged data elements that include a patient data element having information corresponding to a patient associated with the corresponding image data, a study or series data element that identifies a study or series associated with the corresponding image data, a modality data element that includes information about an imaging modality associated with the image data, and an image data element that includes pixel data information associated with the corresponding image data;

an image administration server for the management of the image data; and a local database configured to store the metadata corresponding to the image data acquired by the modality of the satellite;

and wherein the system additionally comprises:

a central database to administer the acquired image data;

a central long-term storage for long-term storage of the acquired image data;

a file server that is configured to:

replicate the image data having been acquired by the modality, and to store the replicated image data in the central database; and replicate the metadata corresponding to the acquired image data and stored in the local database, and to store the replicated metadata in the central database; and a processor that is configured to filter the replicated metadata to remove one or more of the data elements of the replicated metadata to generate partial metadata that corresponds to the image data acquired by the modality of the satellite and includes a subset of the data elements of the metadata, the filtering of the replicated metadata including determining a hierarchy level of the hierarchically arranged data elements of the replicated metadata, and removing one or more data elements from the replicated metadata up to the hierarchy level of the hierarchically arranged data elements, wherein the file server is further configured to further replicates the partial metadata and store the replicated partial metadata in respective local databases of the other satellites of the plurality of satellites not having acquired the image data corresponding to the partial metadata.

18. A system as claimed in claim 17, wherein the plurality of satellites comprise a local short-term storage, the short-term storage being configured to store the pixel data of the image data locally acquired by the respective modality.

19. A system as claimed in claim 17, wherein the system comprises one or more additional central databases, and wherein the file server is further configured to replicate the metadata between the central database and the one or more additional central databases.

20. A system as claimed in claim 19, wherein the central database and/or the one or more additional central databases is/are respectively attached to one or more of the plurality of satellites.

21. A method for storing medical image data in a distributed, computer-based system of a clinical facility comprising a plurality of satellites, wherein a satellite of the plurality of satellites comprises at least one modality, an image processing, image administration and archiving system, a short-term storage cache having fast access speeds, and a short-term storage, and wherein the clinical facility comprises a central database for the administration of image data and a central long-term storage for long-term storage; the method comprising:

acquiring image data at the modality of a satellite of the plurality of satellites, the image data including hierarchically arranged metadata having data elements that include a patient data element having information corresponding to a patient associated with the corresponding image data, a study or series data element that identifies a study or series associated with the corresponding image data, a modality data element that includes information about an imaging modality associated with the image data, and an image data element that includes pixel data information associated with the corresponding image data;

selecting relevant image data from the set of the acquired image data;

locally storing the selected image data in the cache;

locally replicating the metadata corresponding to the acquired image data in the short-term storage;

centrally replicating the acquired image data in the long-term storage;

filtering the replicated metadata in the short-term storage to remove one or more of the data elements of the replicated metadata to generate partial metadata that corresponds to the image data acquired at the satellite and includes a subset of the data elements of the metadata, the filtering of the replicated metadata including determining a hierarchy level of the hierarchically arranged data elements of the replicated metadata, and removing one or more data elements from the replicated metadata up to the hierarchy level of the hierarchically arranged data elements; and decentrally distributing the selected image data and the partial metadata to at least one other satellite of the plurality satellites different from the satellite.

22. A system for storing medical images in memory in a computer-based clinical facility that comprises a plurality of satellites, wherein a satellite of the plurality of satellites comprises:
- a modality configured to acquire image data;
- a Picture Archiving and Communication (PAC) system to administer and manage data; and
- two local short-term storage modules, including a cache and a short-term (ST) storage;

and wherein the system additionally comprises:
- a central database to administer the acquired image data and metadata corresponding to the acquired image data, the metadata including hierarchically arranged data elements that include a patient data element having information corresponding to a patient associated with the corresponding image data, a study or series data element that identifies a study or series associated with the corresponding image data, a modality data element that includes information about an imaging modality associated with the image data, and an image data element that includes pixel data information associated with the corresponding image data;
- a central long-term storage for long-term storage of the acquired image data;
- a file server that replicates the image data acquired by the modality and the corresponding metadata, and stores the replicated image data and the replicated metadata in the central database;
- a processor configured to filter the replicated metadata to remove one or more of the data elements of the replicated metadata to generate partial metadata that corresponds to the image data acquired by the modality of the satellite and includes a subset of the data elements of the metadata, the filtering of the replicated metadata including determining a hierarchy level of the hierarchically arranged data elements of the replicated metadata, and removing one or more data elements from the replicated metadata up to the hierarchy level of the hierarchically arranged data elements;

wherein the file server is further configured to:
- locally replicate the image data acquired by the modality in the ST storage;
- centrally replicate the image data acquired by the modality in the long-term storage; and
- replicate the partial metadata and store the replicated partial metadata in respective ST storages of the local databases of the other satellites of the plurality of satellites whose respective modalities have not acquired the image data corresponding to the partial metadata.

* * * * *